United States Patent
Ohgi et al.

(10) Patent No.: US 7,820,629 B2
(45) Date of Patent: Oct. 26, 2010

(54) GALACTOSE DERIVATIVE, DRUG CARRIER AND MEDICINAL COMPOSITION

(75) Inventors: Tadaaki Ohgi, Tsuchiura (JP); Toshihiro Ueda, Tsukuba (JP); Satoru Sonoke, Tsukuba (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 0 days.

(21) Appl. No.: 12/280,778

(22) PCT Filed: Feb. 28, 2007

(86) PCT No.: PCT/JP2007/053714

§ 371 (c)(1),
(2), (4) Date: Dec. 19, 2008

(87) PCT Pub. No.: WO2007/099981

PCT Pub. Date: Sep. 7, 2007

(65) Prior Publication Data

US 2009/0292005 A1  Nov. 26, 2009

(30) Foreign Application Priority Data

Mar. 1, 2006 (JP) .............................. 2006-054395

(51) Int. Cl.
*A01N 43/04* (2006.01)
*A61K 31/70* (2006.01)

(52) U.S. Cl. ............................ 514/25; 514/23; 514/53; 514/54; 514/61

(58) Field of Classification Search .................. None
See application file for complete search history.

(56) References Cited

U.S. PATENT DOCUMENTS 5,705,188 A * 1/1998 Junichi et al. ............... 424/450

FOREIGN PATENT DOCUMENTS

| EP | 685457 | 12/1995 |
|---|---|---|
| EP | 723972 | 7/1996 |
| EP | 1637144 | 3/2006 |
| JP | 7-188274 A | 7/1995 |
| JP | 9-235292 A | 9/1997 |
| WO | WO-9419314 | 9/1994 |
| WO | WO-2004105774 | 12/2004 |

OTHER PUBLICATIONS

Kitamoto et al. J. Bioscience and Bioengineering (2002), vol. 94, pp. 187-201.*
Rico-Lattes et al. Colloids and Surfaces A: Physicochemical and Engineering Aspects 123-124 (1997) 37-48.*
Rico-Lattes, Isabelle et al. Synthesis of New Sugar-Based Surfactants Having Biological Applications: Key Role of Their Self-Association, Colloids and Surfaces, A: Physicochemical and Engineering Aspects, 1997, vol. 123-124, pp. 37-48.
Andre-Barrnes, Christiane et al. New Double-Chain Surfactants Derived From Glucose and a Lactose—An Alternative to AOT, New Journal of Chemistry, 1995, vol. 19, No. 4, pp. 345-347.
Wilk, Kazimiera A. et al., Preparation and Properties of New Lactose-Based Surfactants, Journal of Surfactants and Detergents, 2001, vol. 4, No. 2, pp. 155-161.
Ricoul, Florence et al., Phase Equilibria and Equation of State of a Mixed Cationic Surfactant-Glycolipid Lamellar System, Langmuir, 1998, vol. 14, No. 10, pp. 2645-2655.
Garrigues, Jean-Christophe et al., Comparative Study for the Incorporation of a New Antifungal Family of Neoglycolipids and Amphotericin B in Monolayers Containing Phospholipids and Cholesterol or Ergosterol, Langmuir, 1998, vol. 14, No. 20, pp. 5968-5971.
Ricoul, Florence et al., An Efficient Method to Determine Isothermal Ternary Phase Diagrams Using Small-Angle X-Ray Scattering, Journal of Physical Chemistry B, 1998, vol. 102, No. 15, pp. 2769-2277.
Rico-Lattes, Isabelle et al., A Short Route to Analogs of Galactosphingolipids Possessing Anti-HIV and Anti-Aspergillus Activity, New Journal of Chemistry, 1995, vol. 19, No. 4, pp. 341-344.

* cited by examiner

*Primary Examiner*—Patrick T Lewis
(74) *Attorney, Agent, or Firm*—McDermott Will & Emery LLP (57) ABSTRACT

The object of the present invention is to provide a novel and useful galactose derivative, which is a component of a drug carrier by which a medicine can be efficiently transferred into the liver, a drug carrier comprising the derivative, and a pharmaceutical composition comprising the drug carrier and a medicine.

The present invention relates to a galactose derivative represented by the following general formula (I) a drug carrier comprising the derivative and a cationic lipid, and a pharmaceutical composition comprising the carrier and a medicine (preferably a double-stranded RNA, a double-stranded DNA, an oligo nucleic acid).

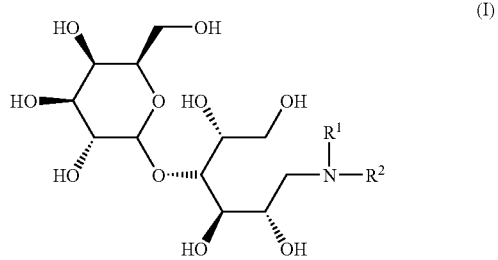

(I)

wherein, $R^1$ represents hydrogen, an alkyl having 1 to 10 carbons which may be substituted or 1-(D)-deoxylactito-1-yl; $R^2$ represents a saturated or unsaturated fatty acid residue having 10 to 30 carbon atoms.

13 Claims, 6 Drawing Sheets

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial sequence
<220> FEATURE:
<223> OTHER INFORMATION: synthesized DNA/RNA; a strand concerning Test
      Example 1, wherein 2 nucleotides of 3'-terminus are constructed
      with DNA, and the rest are RNA.

<400> SEQUENCE: 1
cuuacgcuga guacuucgat t                                          21

<210> SEQ ID NO 2
<211> LENGTH: 21
<212> TYPE: DNA
<213> ORGANISM: Artificial sequence
<220> FEATURE:
<223> OTHER INFORMATION: synthesized DNA/RNA; a strand concerning Test
      Example 1, wherein 2 nucleotides of 3'-terminus are constructed
      with DNA, and the rest are RNA.

<400> SEQUENCE: 2
ucgaaguacu cagcguaagt t                                          21

<210> SEQ ID NO 3
<211> LENGTH: 21
<212> TYPE: DNA
<213> ORGANISM: Artificial sequence
<220> FEATURE:
<223> OTHER INFORMATION: synthesized DNA/RNA; a strand concerning Test
      Example 2, wherein 2 nucleotides of 3'-terminus are constructed
      with DNA, and the rest are RNA.

<400> SEQUENCE: 3
guaguguugg gucgcgaaat t                                          21

<210> SEQ ID NO 4
<211> LENGTH: 21
<212> TYPE: DNA
<213> ORGANISM: Artificial sequence
```

```
-continued

<220> FEATURE:
<223> OTHER INFORMATION: synthesized DNA/RNA; a strand concerning Test
      Example 2, wherein 2 nucleotides of 3'-terminus are constructed
      with DNA, and the rest are RNA.

<400> SEQUENCE: 4
guaguguugg gucgcgaaat t                                              21

<210> SEQ ID NO 5
<211> LENGTH: 21
<212> TYPE: DNA
<213> ORGANISM: Artificial sequence
<220> FEATURE:
<223> OTHER INFORMATION: synthesized DNA/RNA; a strand concerning Test
      Example 4, wherein 2 nucleotides of 3'-terminus are constructed
      with DNA, and the rest are RNA.

<400> SEQUENCE: 5
ggaguacccu gaugagauct t                                              21

<210> SEQ ID NO 6
<211> LENGTH: 21
<212> TYPE: DNA
<213> ORGANISM: Artificial sequence
<220> FEATURE:
<223> OTHER INFORMATION: synthesized DNA/RNA; a strand concerning Test
      Example 4, wherein 2 nucleotides of 3'-terminus are constructed
      with DNA, and the rest are RNA.

<400> SEQUENCE: 6
gaucucauca ggguacucct t                                              21
```

GALACTOSE DERIVATIVE, DRUG CARRIER AND MEDICINAL COMPOSITION

CROSS-REFERENCE TO RELATED APPLICATIONS

This is a U.S. national phase application under 35 U.S.C. §371 of International Patent Application No. PCT/JP2007/053714, filed Feb. 28, 2007, and claims the benefit of Japanese Patent Application No. 2006-054395, filed Mar. 1, 2006. Both the international and priority applications are incorporated by reference herein in their entirety. The International Application published in Japanese on Sep. 7, 2007 as International Publication No. WO 2007/099981 A1 under PCT Article 21(2).

FIELD OF THE INVENTION

The present invention relates to a galactose derivative, a drug carrier and a pharmaceutical composition.

BACKGROUND ART

On the surface of hepatocytes, there is a receptor recognizing asialoglycoproteins. The receptor recognizes the galactose residue of asialoglycoproteins, and has a role in the uptake of asialoglycoproteins by hepatocytes (for example, see M. Spiess, "Biochemistry", 1990, vol. 29, p. 10009-10018).

With such a substrate specificity, it has been studied to improve the liver-targeting of liposomes by way of adding galactose to lipid components of the liposomes. However, none of the studies brought fully satisfactory results (for example, see JP-A H06-271597 and JP-A H09-235392).

On the other hand, in recent years, utilization of a nucleic acid called short interfering RNA (hereinafter referred to as "siRNA") with RNA interference (hereinafter referred to as "RNAi") as a medicine is noticed, and is investigated actively (for example, see WO 02/055692 Pamphlet and WO 02/055693 Pamphlet). siRNA is hard to transfer into cells of a human body if it is administrated alone, and it is necessary to administrate siRNA by embedding it in a suitable carrier, or the like.

DISCLOSURE OF THE INVENTION

Problem to be Solved by the Invention

A main object of the present invention is to provide a novel and useful galactose derivative, a drug carrier comprising the galactose derivative as an essential component, and a pharmaceutical composition comprising the drug carrier including a medicine.

Means to Solve the Problem

The present inventors have conducted extensive researches to find that a drug carrier of which one of the components is a galactose derivative having a particular structure makes a significant improvement in the liver-targeting and the pharmaceutical effect of the included medicine, and have accomplished the present invention.

The present invention can include, for example, inventions illustrated in the following items 1 to 3.

Item 1

A galactose derivative represented by the following general formula (I) (hereinafter-referred to as "the derivative of the present invention"),

[CHEM. 1]

$$
\text{(I)}
$$

(structure shown)

wherein, $R^1$ represents hydrogen, an alkyl having 1 to 10 carbons which may be substituted or 1-(D)-deoxylactito-1-yl; $R^2$ represents a saturated or unsaturated fatty acid residue having 10 to 30 carbon atoms.

Item 2

A drug carrier which comprises a galactose derivative of the above item 1 and a cationic lipid as essential components (hereinafter referred to as "the carrier of the present invention").

Item 3

A pharmaceutical composition which comprises the drug carrier of the above item 2 including a medicine (hereinafter referred to as "the composition of the present invention").

The alkyl having 1 to 10 carbon atoms according to $R^1$ is not particularly limited to the form of straight or branched chain, but can include, for example, methyl, ethyl, n-propyl, isopropyl, n-butyl, isobutyl, sec-butyl, tert-butyl, pentyl, hexyl, heptyl, octyl, nonyl and decyl. Among them, the alkyl having 1 to 4 carbon atoms is preferable, and methyl and ethyl are particularly preferable. Examples of the substituted alkyl can include alkoxyalkyl and halogenated alkyl.

Examples of the alkoxyalkyl can include methoxymethyl, methoxyethyl, ethoxymethyl and ethoxyethyl. Among them, the alkoxyalkyl having 1 to 4 carbon atoms is preferable, and methoxyethyl and ethoxyethyl are particularly preferable. The alkyl moiety of the halogenated alkyl is defined as the same as the above alkyl. In addition, examples of the halogen moiety of the halogenated alkyl can include fluorine, chlorine and bromine. Specifically, the halogenated alkyl can include chloro methyl, chloro ethyl, fluoro methyl, bromo methyl and trifluoromethyl.

Examples of the saturated fatty acid residue having 10 to 30 carbon atoms according to $R^2$ can include caproyl, lauroyl, myristoyl, palmitoyl, stearoyl, arachidoyl, behenoyl, lignoceroyl, cerotoyl, montanoyl and melisoyl. Among them, the saturated fatty acid residue having 10 to 20 carbon atoms is preferable, and stearoyl is particularly preferable. In addition, examples of the unsaturated fatty acid residue having 10 to 30 carbon atoms can include oleoyl, linoleoyl, arachidonoyl and nervonoyl. Among them, the unsaturated fatty acid residue having 10 to 20 carbon atoms is preferable, and oleoyl is particularly preferable.

Examples of the preferred derivative of the present invention can include N-[1-(D)-deoxylactito-1-yl]oleamide and N,N-di[1-(D)-doxylactito-1-yl]oleamide.

BRIEF DESCRIPTION OF THE DRAWINGS

[FIG.1]

[FIG.2]

[FIG.3]

[FIG.4]

[FIG.5]

[FIG.6]

BEST MODE FOR CARRYING OUT THE INVENTION

I. Process of Producing the Derivative of the Present Invention

The derivative (I) of the present invention can be produced by reacting an amine derivative represented by the following general formula (1) with a carboxylic acid derivative represented by the following general formula (2) in the presence of a condensing agent after dissolving them in a suitable solvent. The suitable solvent is not specifically limited unless it is involved in the reaction, and can include, for example, halogenated hydrocarbons (for example, dichloromethane, chloroform, carbon tetrachloride, and 1,2-dichloroethane), acetonitrile, dimethylformamide and solvent mixtures thereof. Examples of the condensing agent can include N,N'-dicyclohexylcarbodiimide, 1-ethyl-3-(3-dimethylaminopropyl)carbodiimide and 1-hydroxybenzotriazole. The reaction temperature is preferably in the range of 0 to 80° C. In addition, the reaction time varies depending on the kind of raw materials used and the reaction temperature applied, and is preferably in the range of 1 to 30 hours.

[CHEM. 2]

(wherein $R^1$ and $R^2$ are defined as the same as the above-mentioned.)

The amine derivative (1) wherein $R^1$ is hydrogen or 1-(D)-deoxylactito-1-yl can be produced by dissolving D-(+)-lactose (3) and a suitable ammonium salt (for example, ammonium tetraborate tetrahydrate, ammonium acetate, ammonium carbonate) in a suitable solvent and reacting them with a reducing agent under an acidic condition. The suitable solvent is not specifically limited unless it is involved in the reaction, and can include, for example, water, alcohols (for example, methanol, ethanol, isopropyl alcohol), halogenated hydrocarbon (for example, dichloromethane, dichloroethane, chloroform) and solvent mixtures thereof. Examples of the acid can include acetic acid, hydrochloric acid and tosic acid. Examples of the reducing agent can include sodium borohydride, sodium cyano borohydride and lithium aluminum hydride. The reaction temperature is preferably in the range of 0 to 80° C. In addition, the reaction time varies depending on the kind of raw materials used and the reaction temperature applied, and is preferably in the range of 1 to 100 hours.

In case where the amine derivative (1) wherein $R^1$ is hydrogen is produced, the ammonium salt may be used suitably within a range of from 1 to 10 equivalents relative to 1 equivalent of D-(+)-lactose. In case where the amine derivative (1) wherein $R^1$ is 1-(D)-deoxylactito-1-yl is produced, D-(+)-lactose may be used suitably in an amount of at least 2 equivalents relative to 1 equivalent of the ammonium salt.

[CHEM. 3]

(wherein R³ represents hydrogen or 1-(D)-deoxylactito-1-yl.)

The amine derivative (1) wherein R¹ is an optionally substituted alkyl having 1 to 10 carbon atoms can be produced according to the above-mentioned production method for the amine derivative (1) wherein R¹ is hydrogen or 1-(D)-deoxylactito-1-yl with the use of an optionally substituted alkyl amine having 1 to 10 carbon atoms in place of the ammonium salt.

The alkyl moiety of the alkylamine is not particularly limited to the form of straight or branched chain, and can include, for example, methyl, ethyl, n-propyl, isopropyl, n-butyl, isobutyl, sec-butyl, tert-butyl, pentyl, hexyl, heptyl, octyl, nonyl and decyl. Among them, the straight or branched alkyl having 1 to 4 carbon atoms is preferable, and methyl and ethyl are particularly preferable. Examples of the substituted alkylamine can include alkoxyamine. Examples of the alkoxyamine can include methoxymethylamine, methoxyethylamine, ethoxymethylamine and ethoxyethylamine.

[CHEM. 4]

(wherein, R⁴ represents an optionally substituted alkyl having 1 to 10 carbon atoms.)

The derivative (I) of the present invention wherein R¹ is hydrogen can also be produced according to the above-mentioned production method for the derivative (I) of the present invention with the use of an amine derivative containing an amine derivative (1) where R¹ is hydrogen and an amine derivative (1) where R¹ is 1-(D)-deoxylactito-1-yl followed by an extraction of the product with a suitable solvent after the reaction. The solvent to be used is not specifically limited, and can include, for example, water, alcohols (for example, methanol, ethanol, isopropyl alcohol), halogenated hydrocarbon (for example, dichloromethane, dichloroethane, and chloroform) and solvent mixtures thereof.

II. The Carrier of the Present Invention

The carrier of the present invention includes the derivative of the present invention and a cationic lipid as essential components, and has a property of intracellularly delivering a medicine as described below. Specifically, the carrier of the present invention can take the form of a liposome, a fat emulsion or the like.

The cationic lipid which is an essential component of the carrier of the present invention is not particularly limited insofar as it is pharmaceutically acceptable cationic lipid, and can include, for example, 2-O-(2-diethylaminoethyl)carbamoyl-1,3-o-dioleoyl glycerol, N-{1-(2,3-dioleyloxy)propyl}-N,N,N-trimethylammonium chloride, dimethyl dioctadecyl ammonium bromide, 1,2-dimyristyloxypropyl-3-dimethyl-hydroxy ethylammonium bromide, N,N',N'',N'''-tetramethyl-N,N',N'',N'''-tetrapalmityl spermine and 2,3-dioleyloxy-N-{2-(spermine carboxamido)ethyl}-N,N-dimethyl-1-propanaminium trifluoroacetate. These can be used alone or as a mixture of two or more thereof. Among them, 2-O-(2-diethylaminoethyl)carbamoyl-1,3-O-dioleoyl glycerol is particularly preferable.

The formulating ratio of the derivative of the present invention to the cationic lipid in the carrier of the present invention may suitably be in the range of 0.01 to 10 parts, preferably in the range of 0.05 to 5 parts, and more preferably in the range of 0.5 to 3 parts by weight of the derivative to 1 part by weight of the cationic lipid.

Other than the derivative of the present invention and the cationic lipid which are essential components of the carrier of the present invention, a phospholipid can further be added. The phospholipid is not particularly limited insofar as it is a pharmaceutically acceptable lipid, and can include, for example, phosphatidylcholine, phosphatidylethanolamine, phosphatidylinositol, phosphatidyl serine, sphingomyelin, lecithin, dipalmitoylphosphatidylcholine, distearoyl phosphatidylcholine and dipalmitoyl phosphatidyl glycerol.

These can be used alone or as a mixture of two or more thereof. Among them, egg yolk phosphatidylcholine, egg yolk lecithin and soybean lecithin are particularly preferable.

When the phospholipid is further added, the formulating ratio of the derivative of the present invention to the phospholipid in the carrier of the present invention may suitably be in the range of 0.01 to 100 parts, preferably in the range of 0.1 to 10 parts, more preferably in the range of 0.3 to 2 parts by weight of the derivative to 1 part by weight of the phospholipid. In addition, the sum of the derivative of the present invention and the phospholipid may suitably be in the range of 0.01 to 10 parts, preferably in the range of 0.05 to 5 parts, more preferably in the range of 0.5 to 3 parts by weight to 1 part by weight of the cationic lipid.

The aqueous dispersion of the carrier of the present invention can be prepared by mixing the derivative of the present invention and a cationic lipid, or the derivative of the present invention, a cationic lipid and a phospholipid, and then dispersing the mixture in an aqueous solution. A machine such as a supersonic dispersing device, an emulsifying dispersion machine and the like may appropriately be used for the dispersion processing.

III. The Composition of the Present Invention

Examples of a medicine used in the composition of the present invention can include water-soluble anionic compounds, antitumor agents, antiviral agents and antibiotics. Specifically, it can include nucleic acid compounds such as double-stranded RNAs, double-stranded DNAs and oligo nucleic acids; acidic saccharides such as heparin sulfate and dextran sulfate; cytokines, second messengers such as cyclic AMP, ATP, and IP3; penicillins and cephalosporins; vitamins such as vitamin C and retinols; other known acidic group-containing drugs, interferons ($\alpha,\beta,\gamma$), interleukins (IL-1, IL-2), colony stimulating factor (CSF), tumor necrosis factor (TNF), levamisole, bestatin, retinoic acid, 5-fluorouracil (5-FU), cytosine arabinoside (Ara-C), adenine arabinoside (Ara-A), cisplatin (CDDP), cyclophosphamide, azidothymidine (AZT) and the like.

Examples of the double-stranded RNA can include the followings.
1. Homopolymer/homopolymer complexes polyinosinic acid/polycytidylic acid, polyinosinic acid/poly(5-bromo cytidylic acid), polyinosinic acid/poly(2-thio cytidylic acid), poly(7-deaza inosinic acid)/polycytidylic acid, poly(7-deaza inosinic acid)/poly(5-bromo cytidylic acid), poly(2'-azide inosinic acid)/polycytidylic acid, polyinosinic acid/poly(cytidine-5'-thiophosphoric acid).
2. Homopolymer/copolymer complexes polyinosinic acid/poly(cytidylic acid—uridine acid), polyinosinic acid/poly(cytidylic acid—4-thiouridine acid).
3. Synthetic nucleic acid/polycation complexes polyinosinic acid/polycytidylic acid/poly-L-lysine.
4. Others polyinosinic acid/poly(1-vinyl cytidylic acid).

The oligo nucleic acid can include an RNA, a DNA and derivatives thereof which have 10 to 50 nucleic acid bases, preferably 15 to 30 nucleic acid bases, and more preferably 18 to 25 nucleic acid bases in one molecule. The oligo nucleic acids can include, for example, an siRNA, a micro RNA (miRNA), a short hairpin RNA (shRNA), an antisense DNA, an antisense RNA, a DNA enzyme, a ribozyme, an aptamer and a non-coding RNA.

The above oligo nucleic acid is not limited to the naturally occurring type, and it is possible to modify at least a part of a nucleotide, such as a sugar and a phosphate backbone constituting the nucleotide, in order to enhance in vivo stability such as a nuclease resistance. Examples of the modification may include a modification of the 2'-position of the ribose, a modification of positions other than 2'-position of the ribose and a modification of the phosphate backbone. The modification of 2'-position of a ribose includes replacement of 2'-hydroxy group of the ribose with H, $OR^5$, $R^5$, $R^6OR^5$, SH, $SR^5$, $NH_2$, $NHR^5$, $N(R^5)_2$, $N_3$, CN, F, Cl Br, I, etc., wherein $R^5$ represents alkyl or aryl and $R^6$ represents alkylene.

The alkyl of $R^5$ is not particularly limited to the form of straight or branched chain, and can include, for example, alkyl having 1 to 6 carbon atoms. Specifically, it can include methyl, ethyl, n-propyl, isopropyl, n-butyl, isobutyl, sec-butyl, tert-butyl, n-pentyl, isopentyl, neopentyl, tert-pentyl, n-hexyl and isohexyl. The alkyl may be substituted by 1 to 3 substituents which can be selected from the group consisting of halogen, alkyl, alkoxy, cyano, nitro and the like. Examples of the halogen may include fluorine, chlorine, bromine and iodine. The alkyl may include the same groups described above. The alkoxy is not particularly limited to the form of straight or branched chain, and can include, for example, alkoxy having 1 to 6 carbon atoms. Specifically, it can include methoxy, ethoxy, n-propoxy, isopropoxy, n-butoxy, isobutoxy, sec-butoxy, tert-butoxy, n-pentyloxy, isopentyloxy, n-hexyloxy and isohexyloxy. Among them, the alkoxy having 1 to 3 carbon atoms is preferable.

Examples of the aryl of $R^5$ may include aryl having 6 to 10 carbon atoms. Specifically, it can include phenyl, alpha-naphthyl and beta-naphthyl. Among them, phenyl is preferable.

The alkylene of $R^6$ is not particularly limited to the form of straight or branched chain, and can include, for example, alkylene having 1 to 6 carbon atoms. Specifically, it can include methylene, ethylene, trimethylene, tetramethylene, pentamethylene, hexamethylene, 2-(ethyl)trimethylene and 1-(methyl)tetramethylene.

The modifications of the other parts of the ribose include a 4'-thio derivative. The modifications of the phosphate backbone include a phosphorothioate derivative, a phosphorodithioate derivative, an alkylphosphonate derivative, a phosphoroamidate derivative, and the like.

The weight ratio of the carrier of the present invention to the medicine in the composition of the present invention (the carrier of the present invention/the medicine) depends on the type of the medicine, the formulating ratio of the derivative of the present invention to the cationic lipid in the carrier of the present invention and so on, and the ratio may suitably be in the range of 0.01 to 1000, preferably in the range of 10 to 300, and more preferably in the range of 100 to 200. Further, when the included medicine is an oligo nucleic acid, the ratio may suitably be in the range of 0.01 to 100, preferably in the range of 1 to 30, and more preferably in the range of 10 to 20.

In the composition of the present invention, pharmaceutically acceptable additives can be optionally blended besides the carrier of the present invention mentioned above and the medicine. The additives may include emulsifying auxiliary agents such as aliphatic acids having 6 to 22 carbon atoms and pharmaceutically acceptable salts thereof, albumin and dextran; stabilizers such as cholesterol and phosphatidic acid; the isotonic agents such as sodium chloride, glucose, maltose, lactose, sucrose, and trehalose; pH adjusters such as hydrochloric acid, sulfuric acid, phosphoric acid, acetic acid, sodium hydroxide, potassium hydroxide, triethanolamine and the like. These can be used alone or as a mixture of two or more thereof. The content of the additives in the compositions of the present invention may suitably be 90% by weight or less, preferably 70% by weight or less, or more preferably 50% by weight or less.

The composition of the present invention is prepared by adding a medicine to the aqueous dispersion of the carrier of the present invention and then stirring properly. In addition, the composition of the present invention can be prepared by adding a medicine in the process for producing the carrier of the present invention. It is possible to add the above additives at an appropriate time of the process either before or after the dispersing.

The composition of the present invention can be prepared in the form of liquid formulations or in the form of freeze-dried preparations. In the case of the liquid formulation, the concentration of the carrier of the present invention in the composition of the present invention may suitably be in the range of 0.001 to 25% (w/v), preferably in the range of 0.01 to 5% (w/v), and more preferably in the range of 0.1 to 2% (w/v).

The above lyophilized preparation can be prepared by freeze-drying the composition of the present invention in the form of a liquid in a conventional method. For example, after adequately sterilizing the composition of the present invention in the form of a liquid, the composition is dispensed into vial containers each in a predetermined amount, and then the complex is subjected to preliminary freezing at about −40 to −20° C. for about 2 hours, followed by a first drying at about 0 to 10° C. under a reduced pressure and a secondary drying at about 15 to 25° C. under a reduced pressure. Thereafter, in general, the vials are filled with nitrogen gas and sealed with stoppers to give lyophilized preparations of the composition of the present invention.

For use, the freeze-dried preparation of the composition of the present invention is ordinarily reconstituted by adding thereto an appropriate solution (reconstituting solution). The reconstituting solution can include water for injection, saline, and other standard infusions. The amount of the reconstituting solution may vary depending on the usage and the like, and is not particularly limited, and an appropriate amount may be 0.5 to 2 times the amount of the original liquid formulation before the freeze-drying or not more than 500 mL.

The composition of the present invention can be used for treating, for example, carcinoma, viral disease, inflammatory disease, metabolic disease and neurologic disease.

The administration route of the composition of the present invention is not particularly limited so long as it is a pharmaceutically acceptable administration route. The route can be selected in accordance with the treatment method therefor. For example, it includes intravenous administration, intra-arterial administration, oral administration, transpulmonary administration, intrastitial administration, percutaneous administration, mucosal administration, rectal administration, intravesical administration, intraperitoned administration, intraocular administration, intracerebral administration, and intrathoracic administration. Among them, intravenous administration, transdermal administration and mucosal administration are preferred. In addition, the pharmaceutical form of the composition of the present invention is not particularly limited, and can be administrated as various types of injections, an oral agent, a drop, an inhalant, an ocular instillation, an ointment, a lotion and a suppository, for example.

Although it is desirable to change the dose of the composition of the present invention as a medicine taking into account the kind of medicine, formulation, patient's conditions such as age and body weight, an administration, and characteristics and seriousness of a disease, the dose is, for example, in the range of 0.01 mg/day/person to 10 g/day/person in terms of the quantity of a medicine for an adult, and preferably in the range of 0.1 mg/day/person to 5 g/day/person. Further, when a medicine contained in the composition of the present invention is an oligo nucleic acid, the dose is generally in the range of 0.1 mg/day/person to 10 g/day/person in terms of the quantity of an oligo nucleic acid for an adult, and preferably in the range of 1 mg/day/person to 5 g/day/person. This dose may vary depending on the type of target disease, the administration method, and the target molecule. Therefore, the dose may be lower than that or may need to be increased in some cases. In addition, the composition may be administered once or several times a day or at intervals of 1 to several days.

EXAMPLE

The present invention will be illustrated more specifically below by referring to Reference Example, Examples, Comparative Example and Test Examples, which are not intended to limit the invention in any way.

Example 1

Synthesis of N-[1-(D)-deoxylactito-1-yl]oleamide

Step 1 Synthesis of a mixture of 1-(D)-deoxylactito-1-yl amine and di[1-(D)-deoxylactito-1-yl]amine 20 g of lactose monohydrate and 22 g of ammonium tetraborate tetrahydrate were suspended in a mixture of 300 mL of methanol, 80 mL of $H_2O$ and 100 mL of acetic acid, then 100 mL of 7% sodium borocyanohydride/methanol solution was added dropwise thereto, and stirred overnight at room temperature. The reaction solution was further stirred at 70° C. for 3 hours, and then the reaction solution was concentrated under reduced pressure. Methanol was added to the residue, then the insolubles were collected by filtration, and the collected insolubles were dried under reduced pressure. The obtained powder was dissolved in a small amount of $H_2O$, the resulting solution was let to pass through a column filled with 500 mL of a cation exchange resin [DOWEX® 50W×2 (pyridinium form)], and the column was fully washed with water. Then 3% aqueous ammonia was let to pass through the column, and the obtained eluate was concentrated under reduced pressure to obtain 12 g of the objective mixture.

Step 2 Synthesis of N-[1-(D)-deoxylactito-1-yl]oleamide 4.9 g of oleic acid and 4.36 g of dicyclohexylcarbodiimide were dissolved in 100 mL of dimethylformamide, and stirred at room temperature for 15 minutes. 5.5 g of the mixture obtained in the above step 1 was added to the reaction solution, and 50 mL of dimethylformamide was further added thereto. The solution was stirred at room temperature for 3 hours, and then concentrated under reduced pressure. A mixture of dichloromethane/methanol (2/1) was added to the residue and centrifuged, and a supernatant of the mixture of dichloromethane/methanol (2/1) was collected. This operation was repeated further three times, and the collected mixture of dichloromethane/methanol (2/1) was concentrated under reduced pressure. 24 mL of $H_2O$, 60 mL of methanol and 30 mL of dichloromethane were added to the residue to dissolve it, and further, 30 mL of dichloromethane and 30 mL of $H_2O$ were added and mixed well. Thereafter, the mixture was centrifuged to obtain the aqueous layer, and it was lyophilized. The residue was purified with silica gel column chromatography to obtain 1.3 g of the objective compound (the derivative of the present invention).

MALDI-TOF Mass (m/z)=608.287 ([M+H]$^+$)
MALDI-TOF Mass (m/z)=630.448 ([M+Na]$^+$)

Example 2

Preparation of the Liquid Dispersion of the Carrier of the Present Invention (1)

In a vial, 60 mg of 2-O-(2-diethylaminoethyl)carbamoyl-1,3-O-dioleoylglycerol, 20 mg of the derivative of the present invention according to Example 1 and 80 mg of egg yolk lecithin (manufactured by WAKO, hereafter the same is applied) were dissolved in 2 mL of chloroform. Then, chloroform was removed under nitrogen gas atmosphere, leaving a thin film on the internal wall of the vial. The vial was then allowed to stand overnight under reduced pressure and, after addition of 4.920 mL of 10% maltose solution and 80 μL of 1 N HCl, the film was dispersed with a vortex mixer. After leaving at 4° C. for 3 hours, the carrier of the present invention at 32 mg/mL was prepared by sonicating for one minute with a microprobe.

Example 3

Preparation of the Liquid Dispersion of the Carrier of the Present Invention (2)

Using 60 mg of 2-O-(2-diethylaminoethyl)carbamoyl-1,3-O-dioleoylglycerol, 40 mg of the derivative of the present invention according to Example 1 and 60 mg of egg yolk lecithin, the liquid dispersion of the carrier of the present invention was prepared in the same manner as in Example 2.

Example 4

Preparation of the Liquid Dispersion of the Carrier of the Present Invention (3)

Using 60 mg of 2-O-(2-diethylaminoethyl)carbamoyl-1,3-O-dioleoylglycerol, 60 mg of the derivative of the present invention according to Example 1 and 40 mg of egg yolk lecithin, the liquid dispersion of the carrier of the present invention was prepared in the same manner as in Example 2.

Example 5

Preparation of the Liquid Dispersion of the Carrier of the Present Invention (4)

Using 60 mg of: 2-O-(2-diethylaminoethyl)carbamoyl-1,3-O-dioleoylglycerol, 80 mg of the derivative of the present invention according to Example 1 and 20 mg of egg yolk lecithin, the liquid dispersion of the carrier of the present invention was prepared in the same manner as in Example 2.

Example 6

Preparation of the Liquid Dispersion of the Carrier of the Present Invention (5)

Using 60 mg of 2-O-(2-diethylaminoethyl)carbamoyl-1,3-O-dioleoylglycerol and 100 mg of the derivative of the present invention according to Example 1, the liquid dispersion of the carrier of the present invention was prepared in the same manner as in Example 2.

Example 7

Preparation of the Liquid Dispersion of the Carrier of the Present Invention (6)

60 mg of 2-O-(2-diethylaminoethyl)carbamoyl-1,3-O-dioleoylglycerol, 20 mg of the derivative of the present invention according to Example 1 and 80 mg of dipalmitoylphosphatidylcholine (manufactured by NOF Corporation, hereafter the same is applied) were added to 4.920 mL of 10% maltose solution and 80 μL of 1 N HCl. Then, the solution was dispersed with a vortex mixer. Afterwards, the carrier of the present invention at 32 mg/mL was prepared by sonicating for one minute with a microprobe.

Example 8

Preparation of the Liquid Dispersion of the Carrier of the Present Invention (7)

Using 60 mg of 2-O-(2-diethylaminoethyl)carbamoyl-1,3-O-dioleoylglycerol, 60 mg of the derivative of the present invention according to Example 1 and 40 mg of dipalmitoylphosphatidylcholine, the liquid dispersion of the carrier of the present invention was prepared in the same manner as in Example 7.

Example 9

Preparation of the Liquid Dispersion of the Carrier of the Present Invention (8)

60 mg of 2-O-(2-diethylaminoethyl)carbamoyl-1,3-O-dioleoylglycerol, 20 mg of the derivative of the present invention according to Example 1 and 80 mg of soybean lecithin (manufactured by WAKO, hereafter the same is applied) were added to 4.920 mL of 0.9% NaCl solution and 80 μL of 1 N HCl. Then, the solution was dispersed with a vortex mixer. After leaving at 4° C. for 3 hours, the carrier of the present invention at 32 mg/mL was prepared by sonicating for one minute with a microprobe.

Example 10

Preparation of the Liquid Dispersion of the Carrier of the present invention (9)

Using 60 mg of 2-O-(2-diethylaminoethyl)carbamoyl-1,3-O-dioleoylglycerol, 60 mg of the derivative of the present invention according to Example 1 and 40 mg of soybean lecithin, the liquid dispersion of the carrier of the present invention was prepared in the same manner as in Example 9.

Example 11

Preparation of the Liquid Dispersion of the Carrier of the Present Invention (10)

60 mg of 2-O-(2-diethylaminoethyl)carbamoyl-1,3-O-dioleoylglycerol, 20 mg of the derivative of the present invention according to Example 1 and 80 mg of distearoylphosphatidylcholine (manufactured by NOF Corporation, hereafter the same is applied) were added to 4.920 mL of 5% D-mannitol solution and 80 μL of 1 N HCl. Then, the solution

Example 12

Preparation of the Liquid Dispersion of the Carrier of the Present Invention (11)

Using 60 mg of 2-O-(2-diethylaminoethyl)carbamoyl-1,3-O-dioleoylglycerol, 60 mg of the derivative of the present invention according to Example 1 and 40 mg of distearoylphosphatidylcholine, the liquid dispersion of the carrier of the present invention was prepared in the same manner as in Example 11.

Example 13

Preparation of the Liquid Dispersion of the Carrier of the present invention (12)

60 mg of 2-O-(2-diethylaminoethyl)carbamoyl-1,3-O-dioleoylglycerol, 20 mg of the derivative of the present invention according to Example 1 and 80 mg of dipalmitoylphosphatidylglycerol (manufactured by NOF Corporation, hereafter the same is applied) were added to 4.920 mL of 5% glucose solution and 80 µL of 1 N HCl. Then, the solution was dispersed with a vortex mixer. After leaving at 4° C. for 3 hours, the carrier of the present invention at 32 mg/mL was prepared by sonicating for one minute with a microprobe.

Example 14

Preparation of the Liquid Dispersion of the Carrier of the Present Invention (13)

Using 60 mg of 2-O-(2-diethylaminoethyl)carbamoyl-1,3-O-dioleoylglycerol, 60 mg of the derivative of the present invention according to Example 1 and 40 mg of dipalmitoylphosphatidylglycerol, the liquid dispersion of the carrier of the present invention was prepared in the same manner as in Example 13.

Comparative Example 1

Preparation of the Liquid Dispersion of the Comparative Carrier (1)

Using 60 mg of 2-O-(2-diethylaminoethyl)carbamoyl-1,3-O-dioleoylglycerol and 100 mg of egg yolk lecithin, the liquid dispersion of the comparative carrier was prepared in the same manner as in Example 2.

Comparative Example 2

Preparation of the Liquid Dispersion of the Comparative Carrier (2)

Using 60 mg of 2-O-(2-diethylaminoethyl)carbamoyl-1,3-O-dioleoylglycerol and 100 mg of dipalmitoylphosphatidylcholine, the liquid dispersion of the comparative carrier was prepared in the same manner as in Example 7.

Comparative Example 3

Preparation of the Liquid Dispersion of the Comparative Carrier (3)

Using 60 mg of 2-o-(2-diethylaminoethyl)carbamoyl-1,3-O-dioleoylglycerol and 100 mg of soybean lecithin, the liquid dispersion of the comparative carrier was prepared in the same manner as in Example 9.

Comparative Example 4

Preparation of the Liquid Dispersion of the Comparative Carrier (4)

Using 60 mg of 2-O-(2-diethylaminoethyl)carbamoyl-1,3-O-dioleoylglycerol and 100 mg of distearoylphosphatidylcholine, the liquid dispersion of the comparative carrier was prepared in the same manner as in Example 11.

Comparative Example 5

Preparation of the Liquid Dispersion of the Comparative Carrier (5)

Using 60 mg of 2-O-(2-diethylaminoethyl)carbamoyl-1,3-O-dioleoylglycerol and 100 mg of dipalmitoylphosphatidylglycerol, the liquid dispersion of the comparative carrier was prepared in the same manner as in Example 13.

Test Example 1

Evaluation of Liver-Targeting (1) Preparation of a Nucleic Acid Solution

A nucleic acid solution containing a tritium-labeled siRNA composed of an oligo RNA having a sequence of SEQ ID NO 1 and an oligo RNA having a sequence of SEQ ID NO 2 was prepared by introducing tritium-labeled [2,5',8-3H]adenosine 5'-triphosphate ammonium salt (manufactured by Amersham Bioscience), using in-vitro Transcription T7 Kit (manufactured by Takara Bio). The siRNA concentration in the nucleic acid solution was 20 µM. The specific activity was $6.4 \times 10^5$ dpm/µg.

341.25 µL of a nucleic acid solution containing 20 µM of a tritium-unlabeled siRNA composed of an oligo RNA having a sequence of SEQ ID NO 1 and an oligo RNA having a sequence of SEQ ID NO 2 was added to 8.75 µL of the nucleic acid solution prepared in the above step, thereby preparing a nucleic acid solution having a specific activity of $1.6 \times 10^4$ dpm/µg.

(2) Preparation of a Composition

90 µL of 10% maltose was added to 10 µL of the nucleic acid solution prepared in the above (1) and having a specific activity of $1.6 \times 10^4$ dpm/µg, thereby preparing a nucleic acid solution containing 2 µM of siRNA. The liquid dispersion of the carrier according to Examples 2 to 6 or Comparative Example 1 was diluted with 10% maltose added thereto, thereby preparing 429 µg/mL of the liquid dispersion of the carrier.

To each liquid dispersion of the carrier (429 µg/mL), was added the same amount of the nucleic acid solution (2 µM) and mixed, using a vortex mixer. Then this was statically kept at room temperature for 15 minutes and then ultrasonically processed for 15 seconds, thereby preparing a composition containing 1 µM of siRNA.

(3) Method of Experiment

HuH-7 cells (human hepatoma cell line) were seeded on a 6-well plate at $2.5 \times 10^5$ cells/well, and were incubated for 18 hours at 37° C. under 5% $CO_2$. The medium was exchanged, and then 100 µL of the composition prepared in the above (2) was added to each well so that the final concentration of siRNA was 100 nM, and the incubation was further continued. Eight hours after the addition of the composition, the cells were washed twice with mL of phosphate buffered saline (hereinafter referred to as "PBS"), then the cells were peeled away with 400 µL of trypsin/EDTA (manufactured by SIGMA) and collected in an Eppendorf tube. 800 µL of PBS was further added to the washed well and the remaining cells, if any, were thus completely collected in the same tube as above, thereby confirming no remaining cells therein. After centrifuging at 3000 rpm for 2 minutes, 800 µL of the supernatant was removed, and all the residue was transferred to a scintillation vial. 4 mL of a liquid scintillation cocktail (Emulsifier Scintillator Plus, manufactured by Perkin Elmer) was added to each of the vials and mixed well, and the radioactivity was counted with a liquid scintillation counter (manufactured by Perkin Elmer).

(4) Result

Figure 1:
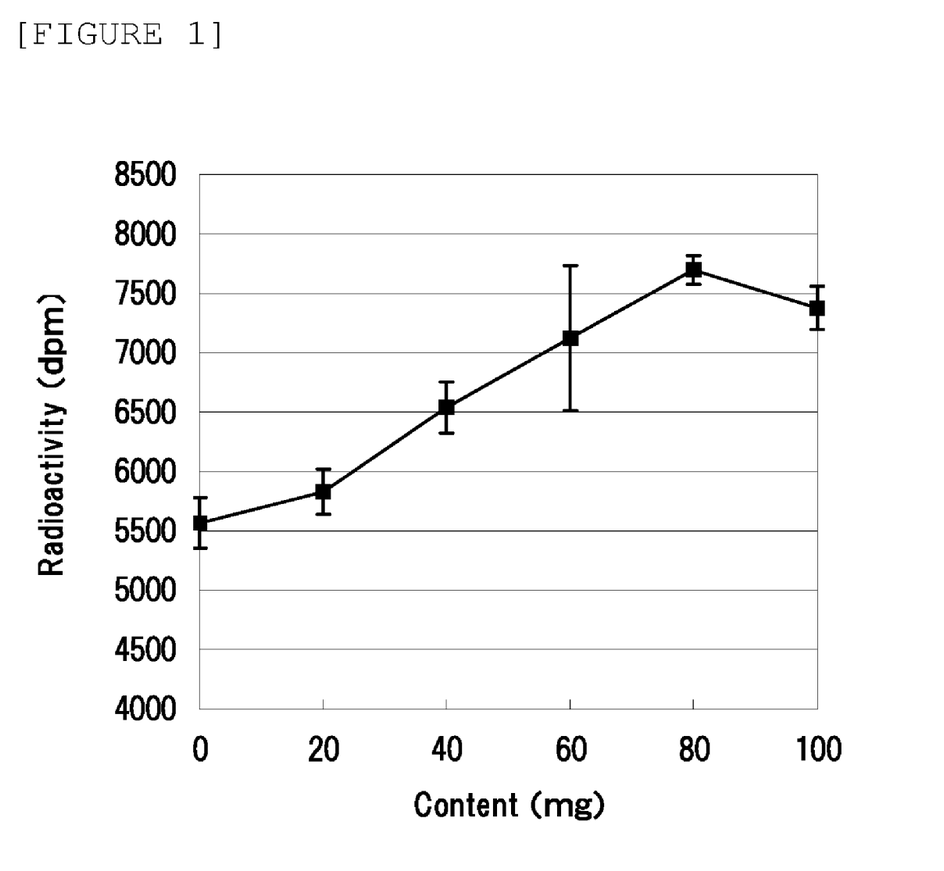
FIG. 1 shows liver-targeting property. The vertical axis indicates the radioactivity (dpm), and the horizontal axis indicates the content (mg) of the derivative of the present invention according to Example 1.

As a result, it was proved that the liver-targeting potency increases depending on the content of the derivative of the present invention according to Example 1, as shown in FIG. 1.

Test Example 2

Evaluation of Pharmacological Activity (1)

The pharmacological activity of a composition of the present invention, containing the carrier of the present invention according to Example 7 or 8 and an siRNA having an HCV replication-inhibiting activity, was tested and evaluated based on the production of a non-structural protein of HCV, NS5A protein taken as the index thereof.

(1) Preparation of a Nucleic Acid Solution

An oligo RNA having a sequence of SEQ ID NO 3 and an oligo RNA having a sequence of SEQ ID NO 4 each were dissolved in water for injection so as to have a concentration of 100 µM, thereby preparing an oligo. RNA stock solution. Then, the two solutions of 20 µL each were mixed in a test tube, and 60 µL of water for injection was added thereto, thereby preparing a nucleic acid solution containing siRNA at 20 µM.

Meanwhile, the synthesis of the above two oligo RNAs was entrusted to Japan Bio Services Co., LTD.

(2) Preparation of a Composition

90 µL of 10% maltose was added to 10 µL of the nucleic acid solution (20 µM) prepared in the above (1), thereby preparing a nucleic acid solution containing siRNA at 2 µM. 98.7 µL of 10% maltose was added to 1.3 µL of the liquid dispersion of the carrier according to Example 7, 8 or Comparative Example 2, thereby preparing a liquid dispersion of the carrier at 428.8 mg/mL.

100 µL of the nucleic acid solution (2 µM) and 100 µL of the liquid dispersion of the carrier (428.8 mg/mL) were mixed in a test tube, then statically left at 4° C. for 5 minutes and thereafter ultrasonically processed to prepare a composition containing siRNA at 1 µM. This composition appropriately diluted by 10% maltose solution was used in the following experiment.

(3) Method of Experiment

HuH-7 cells carrying the replicon of HCV [the details of the cell have been reviewed in the reference (Biochemical and Biophysical Research Communications, 2000, vol. 293, p. 993-999)] were seeded on a 6-well plate at $1 \times 10^5$ cells/well, and were incubated for 20 hours at 37° C. under 5% $CO_2$. Then, 100 µL of the composition prepared in the above (2) was added to each well so that the final concentration of siRNA was 30 nM or 100 nM, and the incubation was further continued for 96 hours under the same condition. The cultured cells were washed with PBS, and then collected to prepare a cell lysate solution.

The cell lysate solution having a total protein content of 5 µg was thermally degraded, then isolated through SDS-PAGE, and electrically transferred to a polyvinylidene difluoride membrane (hereinafter referred to as "PVDF membrane") (manufactured by Millipore). After the transfer, the PVDF membrane was stained with an anti-NS5A polyclonal antibody (manufactured by Viro Gen) and a horseradish peroxidase (hereinafter referred to as "HRP")-labeled anti-rabbit IgG antibody (manufactured by Cell Signaling Technologies). The stained PVDF membrane was processed for chemiluminescence with Chemiluminescence Reagent Plus (manufactured by Perkin Elmer), whereby the emission intensity of the band corresponding to NS5A protein was quantitatively determined and digitalized with an imaging analyzer (manufactured by BioRad). In addition, using an anti-α-actin monoclonal antibody (manufactured by SIGMA) and an HRP-labeled anti-mouse IgG antibody (manufactured by Cell Signaling Technologies), the band intensity corresponding to α-actin protein was also computed in the same manner.

The quantified value of the band corresponding to NS5A protein was divided by the quantified value of the band corresponding to α-actin protein to give the production of NS5A protein per the unit amount of protein.

(4) Evaluation

The evaluation was performed by comparing the production of NS5A protein among the cells treated with respective preparations of the present invention regarding the production of NS5A protein per unit of protein in the cell treated with 10% maltose solution as 100%. The lower production of NS5A protein means the stronger inhibition of the replicon replication.

(5) Result

Figure 2:
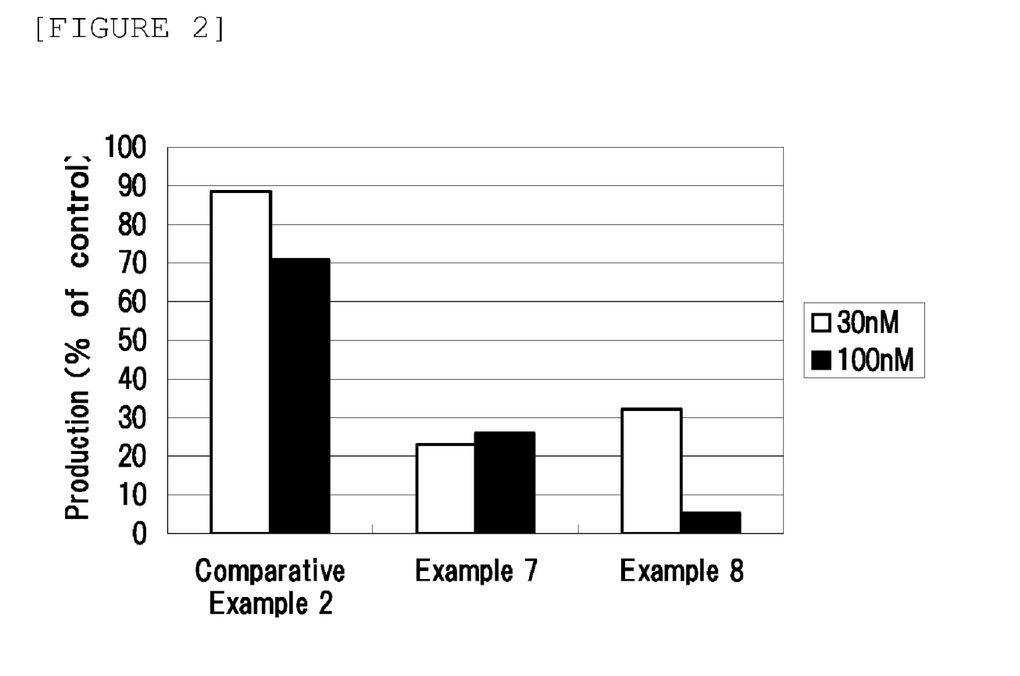
FIG. 2 shows the inhibitory activity on the replication of hepatitis C virus (herein after referred to as "HCV") replicon. The vertical axis indicates the production of NS5A protein relative to 100% control production (% of control). The white bar shows the result of the cells treated with siRNA at a concentration of 30 nM; and the black bar shows the result of the cells treated with siRNA at a concentration of 100 nM.

As shown in FIG. 2, when the composition of the present invention containing the carrier of the present invention according to Example 7 or 8 was used, the replication of HCV replicon was inhibited more strongly as compared with when the carrier according to Comparative Example 2 was used.

Test Example 3

Evaluation of Pharmacological Activity (2)

The pharmacological activity of the composition of the present invention, containing the carrier according to Example 9 or 10 and an siRNA having an HCV replication inhibiting activity, was tested and evaluated based on the production of NPTII protein, a product of neomycin-resistant gene taken as the index thereof.

(1) Preparation of a Composition

The composition containing a siRNA at 1 µM was prepared in the same manner as in Test Example 2 by using the liquid dispersion of the carrier according to Example 9, 10 or Comparative Example 3 and the nucleic acid solution (2 µM) prepared in the above Test Example 2. This composition appropriately diluted by 10% maltose solution was used in the following experiment.

(2) Method of Experiment

HuH-7 cells carrying the replicon of HCV [the details of the cell have been reviewed in the reference (Biochemical and Biophysical Research Communications, 2000, vol. 293, p. 993-999)] were seeded on a 12-well plate at $5 \times 10^4$ cells/well, and were incubated overnight at 37° C. under 5% $CO_2$. The next day, the culture medium was removed from the plate under suction, and 0.9 mL of the culture medium was added. 100 μL of the composition prepared in the above (1) was added to each well so that the final concentration of siRNA was 30 or 100 nM, and the incubation was further continued for 96 hours under the same condition. The cultured cells were washed with PBS, and then collected to prepare a protein extract. The amount of NPTII protein in the protein extract was determined, using a commercially-available test kit (PathoScreen Kit for NPTII, manufactured by Agdia). The preparation of the protein extract was performed by using an extraction buffer attached to the kit. The overall protein content in the extracted protein was measured by a commercially-available kit (BCA Protein Assay Kit, manufactured by Pierce).

(3) Evaluation

The evaluation was performed by comparing the production of NPTII protein among the cells treated with respective preparations of the present invention regarding the production of NPTII protein per unit of protein in the cell treated with 10% maltose solution as 100%. Meanwhile, the lower production of NPTII protein means the stronger inhibition of the replication of HCV replicon.

(4) Result

Figure 3:
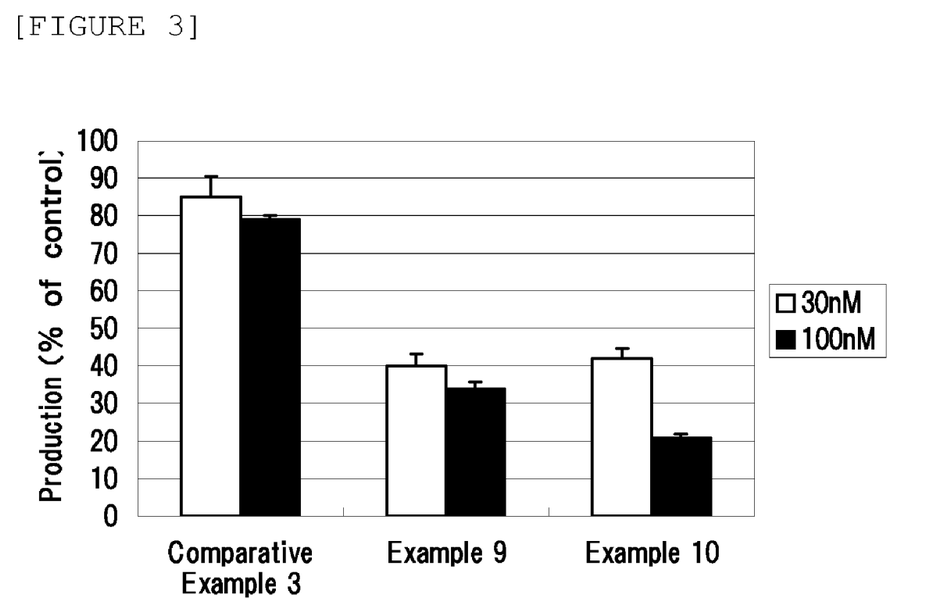
FIG. 3 shows the inhibitory activity on the replication of HCV replicon. The vertical axis indicates the production of neomycin phosphotransferase II protein (hereinafter referred to as "NPTII protein") relative to 100% control production (% of control). The white bar shows the result of the cells treated with siRNA at a concentration of 30 nM; and the black bar shows the result of the cells treated with siRNA at a concentration of 100 nM.

As shown in FIG. 3, when the composition of the present invention containing the carrier of the present invention according to Example 9 or 10 was used, the replication of HCV replicon was inhibited more strongly as compared with when the carrier according to Comparative Example 3 was used.

Test Example 4

Evaluation of Pharmacological Activity (3)

The pharmacological activity of the composition of the present invention, containing the carrier according to Example 11 or 12 and an siRNA against human VEGF-A gene, was tested and evaluated based on the production of a human VEGF-A protein taken as the index thereof.

(1) Preparation of a Composition

An siRNA against human VEGF-A gene (manufactured by Ambion), composed of an oligo RNA having a sequence of SEQ ID NO 5 and an oligo RNA having a sequence of SEQ ID NO 6, was diluted with water for injection, thereby preparing a nucleic acid solution containing siRNA at 20 μM. 90 μL of 10% maltose was added to 10 μL of the nucleic acid solution (20 μM), thereby preparing a nucleic acid solution containing siRNA at 2 μM. 98.7 μL of 10% maltose was added to 1.3 μL of the liquid dispersion of the carrier according to Example 11, 12 or Comparative Example 4, thereby preparing a liquid dispersion of the carrier at 428.8 mg/mL.

100 μL of the nucleic acid solution (2 μM) and 100 μL of the liquid dispersion of the carrier (428.8 mg/mL) were mixed in a test tube, then statically left at 4° C. for 15 minutes and thereafter ultrasonically processed to prepare a composition containing siRNA at 1 μM. This composition appropriately diluted by 10% maltose solution was used in the following experiment.

(2) Method of Experiment

HuH-7 cells were seeded on a 12-well plate at $1\times10^5$ cells/well, and were incubated for 18 hours at 37° C. under 5% $CO_2$. The next day, the culture medium was removed from the plate under suction, and 0.9 mL of the culture medium was added. 100 μL of the composition prepared in the above (1) was added to each well so that the final concentration of siRNA was 30 nM or 100 nM, and the incubation was further continued for 24 hours under the same condition. The culture medium was removed by suction from the culture plate, then 0.9 mL of a medium was added for medium exchange, and the incubation was further continued for 24 hours under the same condition. After the incubation, the amount of the human VEGF-A protein in the culture supernatant was measured by a commercially-available kit (Human VEGF immunoassay kit, manufactured by R & D Systems).

(3) Evaluation

The evaluation was performed by comparing the production of human VEGF-A protein among the cells treated with respective preparations of the present invention regarding the production of human VEGF-A-protein in the cell treated by 10% maltose solution as 100%.

(4) Result

Figure 4:
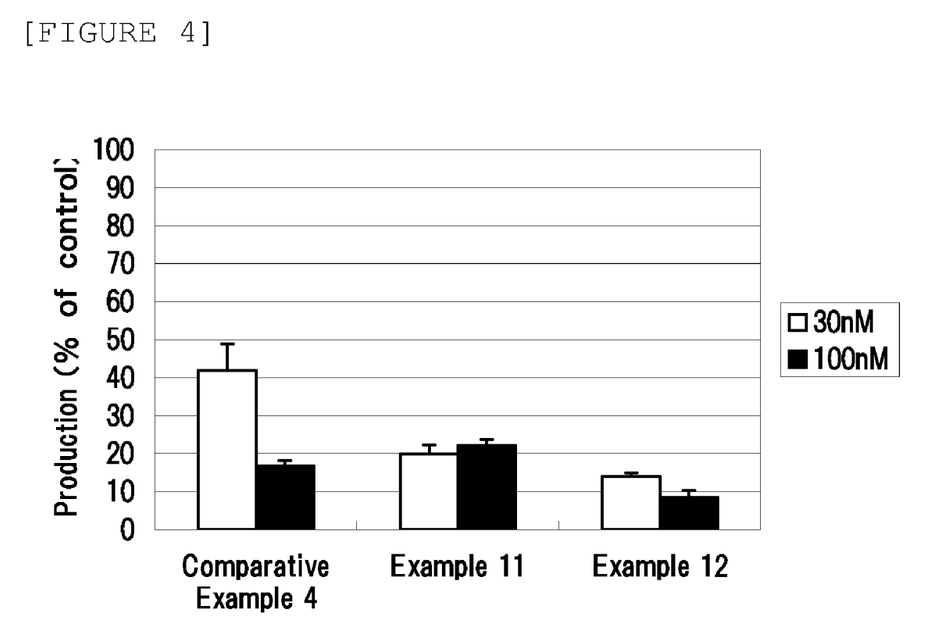
FIG. 4 shows the inhibitory activity on the expression of human VEGF-A protein. The vertical axis indicates the production of human VEGF-A protein relative to 100% control production (% of control). The white bar shows the result of the cells treated with siRNA at a concentration of 30 nM; and the black bar shows the result of the cells treated with siRNA at a concentration of 100 nM.

As shown in FIG. 4, when the composition of the present invention containing the carrier of the present invention according to Example 11 or 12 was used, the production of human VEGF-A protein was inhibited equivalently or more strongly as compared with when the carrier according to Comparative Example 4 was used.

Test Example 5

Evaluation of Pharmacological Activity (4)

The pharmacological activity of the composition of the present invention, containing the carrier according to Example 13 or 14 and an siRNA against human VEGF-A gene, was tested and evaluated based on the production of a human VEGF-A protein taken as the index thereof.

(1) Preparation of a Composition

The composition containing a siRNA at 1 μM was prepared in the same manner as in Test Example 4 by using the liquid dispersion of the carrier according to Example 13, 14 or Comparative Example 5 and the nucleic acid solution (2 μM) prepared in the above Test Example 4. This composition appropriately diluted by 10% maltose solution was used in the following experiment.

(2) Method of Experiment

HepG2 cells (human hepatoma cell line) were seeded on a 12-well plate at $2\times10^5$ cells/well, and were incubated for 18 hours at 37° C. under 5% $CO_2$. The next day, the culture medium was removed from the plate under suction, and 0.9 mL of the culture medium was added. 100 μL of the composition prepared in the above (1) was added to each well so that the final concentration of siRNA was 30 nM or 100 nM, and the incubation was further continued for 24 hours under the same condition. The culture medium was removed by suction from the culture plate, then 0.9 mL of a medium was added for medium exchange, and the incubation was further continued for 24 hours under the same condition. After the incubation, the amount of the human VEGF-A protein in the culture supernatant was measured by a commercially-available kit (Human VEGF immunoassay kit, manufactured by R & D Systems).

(3) Evaluation

The evaluation was performed by comparing the production of human VEGF-A protein among the cells treated with respective preparations of the present invention regarding the production of human VEGF-A protein in the cell treated by 10% maltose solution as 100%.

(4) Result

Figure 5:
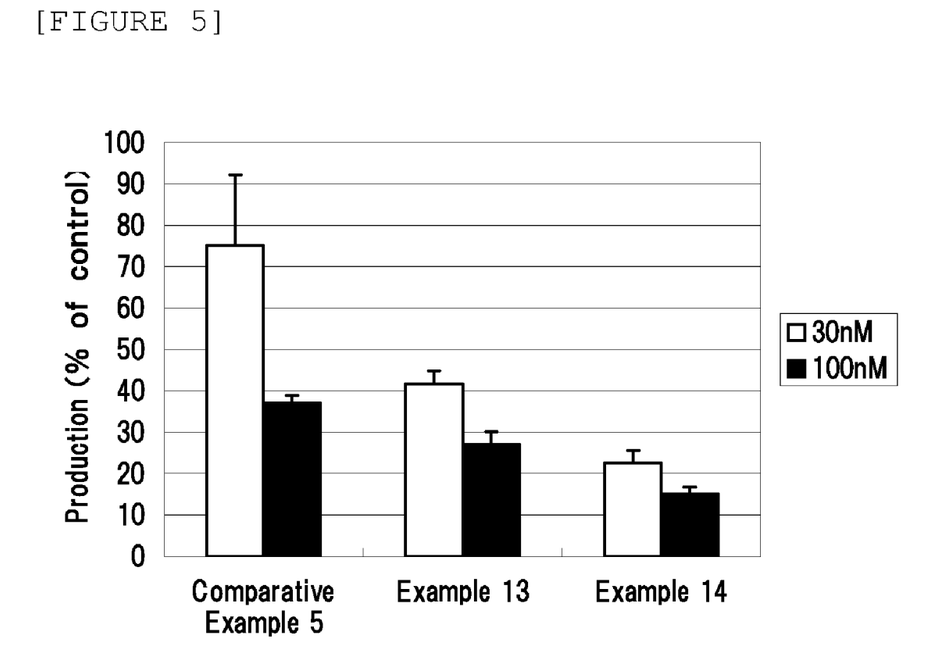
FIG. 5 shows the inhibitory activity on the expression of human VEGF-A protein. The vertical axis indicates the production of human VEGF-A protein relative to 100% control production (% of control). The white bar shows the result of the cells treated with siRNA at a concentration of 30 nM; and the black bar shows the result of the cells treated with siRNA at a concentration of 100 nM.

As shown in FIG. 5, when the composition of the present invention containing the carrier of the present invention according to Example 13 or 14 was used, the production of human VEGF-A protein was inhibited more strongly as compared with when the carrier according to Comparative Example 5 was used.

Test Example 6

Evaluation of Cytotoxicity (1) Preparation of a Composition

The composition containing a siRNA at 1 µM was prepared in the same manner as in Test Example 2 by using the liquid dispersion of the carrier according to Example 2, 4, 6 or Comparative Example 1 and the nucleic acid solution (2 µM) prepared in the above Test Example 2. This composition appropriately diluted by 10% maltose solution was used in the following experiment.

(2) Method of Experiment

HuH-7 cells were seeded on a 96-well plate at $3 \times 10^3$ cells/well, and were incubated for 18 hours at 37° C. under 5% $CO_2$. Then, 11.1 µL of the composition prepared above (1) was added per well so that the final concentration of siRNA was 30 or 100 nM. After incubating for 96 hours under the same condition, the cell number was measured by using a commercial kit (Cell Proliferation Kit II, product of Roche).

(3) Evaluation

The evaluation was performed by comparing cell number among the cells treated with respective preparations of the present invention regarding the cell number of the cell treated by 10% maltose solution as 100%.

(4) Result

Figure 6:
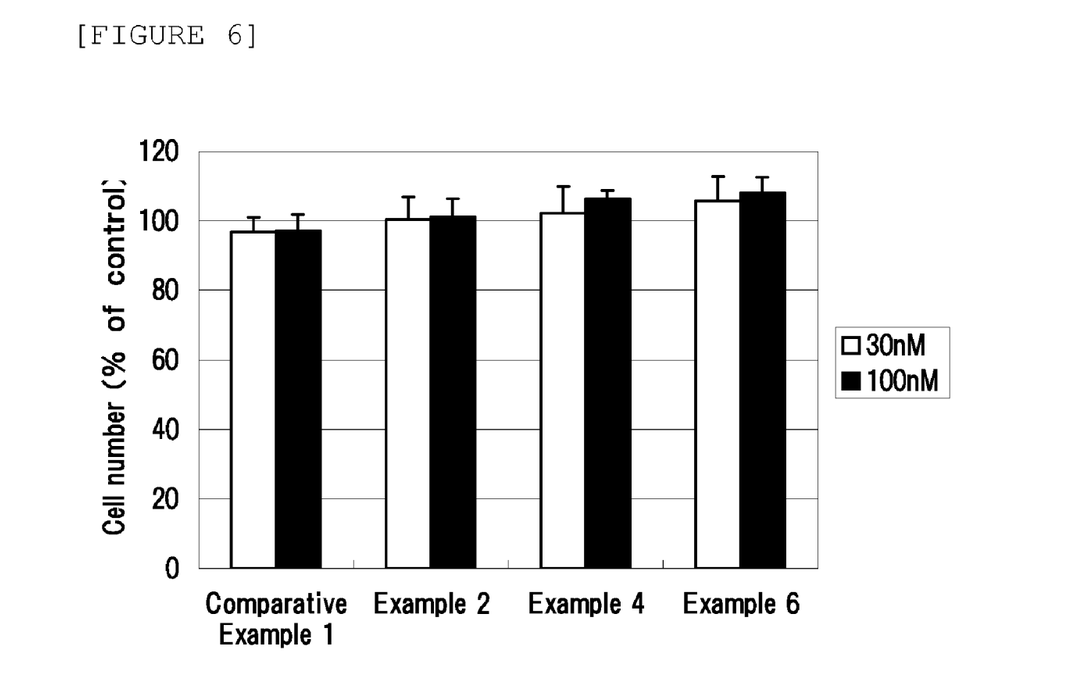
FIG. 6 shows the cytotoxicity. The vertical axis indicates the number of cells relative to 100% control number of cells (% of control). The white bar shows the result of the cells treated with siRNA at a concentration of 30 nM; and the black bar shows the result of the cells treated with siRNA at a concentration of 100 nM.

As shown in FIG. 6, cytotoxicities of the carrier of the present invention according to Example 2, 4 and 6 were approximately the same as that of the carrier according to Comparative example 1.

---

The invention claimed is:

1. A galactose derivative represented by general formula (I)

wherein, $R^1$ represents hydrogen or 1-(D)-deoxylactito-1-yl; and $R^2$ represents a saturated or unsaturated fatty acid residue having 10 to 30 carbon atoms.

2. The galactose derivative according to claim 1, wherein the galactose derivative is N-[1-(D)-deoxylactito-1-yl]oleamide or N,N-di[1-(D)-deoxylactito-1-yl]oleamide.

3. A drug carrier comprising a galactose derivative according to claim 1 and a cationic lipid.

4. The drug carrier according to claim 3, wherein the cationic lipid is 2-O-(2-diethylaminoethyl)carbamoyl-1,3-O-dioleoylglycerol.

5. The drug carrier according to claim 3, further comprising a phospholipid.

6. A pharmaceutical composition comprising a containing the drug carrier according to claim 3, and a medicine.

7. The pharmaceutical composition according to claim 6, wherein the medicine is a double-stranded RNA, a double-stranded DNA, an oligo nucleic acid or a water-soluble anion compound.

8. The pharmaceutical composition according to claim 7, wherein the oligo nucleic acid is a short interfering RNA, a micro RNA, a short hairpin RNA, an antisense DNA, an antisense RNA, a DNA enzyme, a ribozyme, an aptamer, or a non-coding RNA.

9. The pharmaceutical composition according to claim 6, which is used for treating and/or preventing a carcinoma.

10. The pharmaceutical composition according to claim 6, which is used for treating and/or preventing a viral disease.

11. The pharmaceutical composition according to claim 6, which is used for treating and/or preventing a inflammatory disease.

12. The pharmaceutical composition according to claim 6, which is used for treating and/or preventing a metabolic disease.

13. The pharmaceutical composition according to claim 6, which is used for treating and/or preventing a neurologic disease.

* * * * *